(12) United States Patent
Atwood et al.

(10) Patent No.: US 7,169,957 B2
(45) Date of Patent: Jan. 30, 2007

(54) SUBSTANTIALLY SPHERICAL SUPRAMOLECULAR ASSEMBLIES

(76) Inventors: Jerry L. Atwood, 5704 S. Short Line Dr., Columbia, MO (US) 65203; Leonard R. MacGillivray, 103 Oberlin St., Iowa City, IA (US) 52245

( * ) Notice: Subject to any disclaimer, the term of this patent is extended or adjusted under 35 U.S.C. 154(b) by 0 days.

(21) Appl. No.: 10/408,605

(22) Filed: Apr. 7, 2003

(65) Prior Publication Data

US 2004/0014963 A1    Jan. 22, 2004

Related U.S. Application Data

(63) Continuation of application No. 09/319,136, filed on Nov. 9, 1999, now abandoned.

(51) Int. Cl.
*C07C 39/12*    (2006.01)
(52) U.S. Cl. ..................... 568/719; 568/720
(58) Field of Classification Search ............... 568/719, 568/720
See application file for complete search history.

(56) References Cited

OTHER PUBLICATIONS

Leonard R. MacGillivray and Jerry L. Atwood□□A Chiral sperical molecular assembly held together by 60 hydrogen bonds□□□□Nature 389, 469-472 (Oct. 2, 1997).□□*
Peter Timmerman, Willem Verboom, Frank C.J.M. van Veggel, John P.M. van Duynhoven and David N. Reinhoudt□□A Novel Type of Stereoisomerism in Calix[4]arene-Based Carceplexes□□□□Angew. Chem. Int. Ed. Engl. 1994,33,No. 22 pp. 2345-2348.*
Peter Timmerman, Willem Verboom, Frank C.J.M. van Veggel, Willem P. van Hoorn, and David N. Reinhoudt□□An Organic Molecule with a Rigid Cavity of Nanosize Dimensions□□□□Angew. Chem. Int. Ed. Engl. 1994,33,No. 12 pp. 1292-1294.*

* cited by examiner

*Primary Examiner*—Johann Richter
*Assistant Examiner*—Lalitha Nagubandi
(74) *Attorney, Agent, or Firm*—William D. Jackson; Schultz & Associates, P.C.

(57) ABSTRACT

Disclosed are the general principles upon which closed molecular or ionic structural frameworks may be prepared. These frameworks are based upon the self-assembly (wherein the term self-assembly refers to the association of chemical components through inter-component bonds) of n>4 subunits where surface curvature is supplied by edge sharing of subunits.

10 Claims, 7 Drawing Sheets

24.3 Å

| 2  | calix[4]resorcinarene | R = H |
|----|----------------------|-------|
| 2a | C-methylcalix[4]resorcinarene | R = Me |
| 2b | C-undecylcalix[4]resorcinarene | R = undecy |

SUBSTANTIALLY SPHERICAL SUPRAMOLECULAR ASSEMBLIES

This application is a continuation of application Ser. No. 09/319,136, filed Nov. 9, 1999.

BACKGROUND OF THE INVENTION

1. Field of the Invention

The present invention generally relates to the preparation of molecular or ionic supramolecular assemblies having a substantially enclosed volume and a framework structure that mimics a Platonic or Archimedean solid.

2. Related Art

Spontaneous self-assembly processes that lead to discrete spherical arrays are common in Nature. Indeed, spherical viruses (Caspar et al., D. & Klug, A. Physical principles in the construction of regular viruses. *Cold Spring Harb. Symp. Quant. Biol.* 27, 1–24 (1962)) (e.g. hepatitis B) and fullerenes (Kroto et al., H. W., Heath, J. R., O'Brien, S. C., Curl, R. F., Smalley, R. E. $C_{60}$: Buckminster-fullerene. *Nature* 318, 162–163 (1985)) (e.g. $C_{60}$) are well known examples in which noncovalent and covalent forces, respectively, direct the assembly of smaller sub-units (or synthons) into larger superstructures. A common feature of these shell-like architectures is their ability to encapsulate neutral and/or charged guests whose size, shape, and chemical exteriors complement their inner surfaces. (Casjens, S. Nucleic acid packaging by viruses, in *Virus Structure and Assembly* (ed. Casjens, S.) 75–147, Jones and Bartlett, Boston, 1995; Schwarz et al., H., Weiske, T., Bohme, D. K., Hrusdak, J. Exo- and endohedral fullerene complexes in the gas phase, in *Buckminsterfullerenes*, eds. Billups, W. E. & Ciufolini, M. A., 257–283, VCH, New York, 1993, the disclosures of which are incorporated by reference). Their interiors can often be regarded as unique phases of matter (Sherman et al., J. C. & Cram, D. J. Carcerand interiors provide a new phase of matter. *J. Am. Chem. Soc.* 111, 4527–4528 (1989)) capable of controlling the flow of reactants, transients, and products and catalyzing reactions of both chemical and biological relevance. Such properties have inspired the recent emergence of mono- and supramolecular dimeric molecular capsules (Sherman et al.; Garel et al., L, Dutasta, J.-P., Collet, A. Complexation of methane and chlorofluorocarbons by cryp-tophane-A in organic solution. *Angew. Chem. Int. Ed Engl.* 32, 1169–1171 (1993); Timmerman et al., P., Verboom, W., van Veggel, F. C., van Duynhoven, J. P., Reinhoudt, D. N. A novel type of stereoisomerism in calix[4]arene-based carceplexes. *Angew. Chem. Int. Ed Engl.* 33, 2345–2348 (1994); (Kang et al., J. & Rebek, J. Jr. Acceleration of a Diels-Alder reaction by a self-assembled molecular capsule. *Nature* 385, 50–52 (1997); Shimizu et al., K. D., Rebek, J. Jr. Synthesis and assembly of self-complementary calix[4]arenes. *Proc. Natl. Acad. Sci. USA.* 92, 12403–12407 (1995); the disclosures of which are incorporated by reference), many of which have been based upon the head-to-head alignment of bowl-shaped polyaromatic macrocycles such as calix[4]arenes. Despite the synthesis of these pseudo-spherical capsules, however, structural mimicry of frameworks akin to viruses and fullerenes, which are based upon the self-assembly of n>3 sub-units where surface curvature is supplied by edge sharing of regular polygons and/or polygons that exhibit quasi-equivalence, has remained elusive and promises to bear relevance in a number of areas including biology, chemistry, and materials science

SUMMARY OF THE INVENTION

Among the objects of the invention, therefore, is the provision of a supramolecular assembly having a substantially enclosed volume and a framework structure that mimics a Platonic or Archimedean solid.

Briefly, therefore, the present invention is directed to a substantially spherical supramolecular assembly having a substantially enclosed volume and framework structure that mimics a Platonic or Archimedean solid. The supramolecular assembly comprises at least four synthons held together by a combination of carbon-based covalent, non-covalent, and/or coordinate covalvalent bonds provided at least two of the bonds are selected from non-covalent and coordinate covalent bonds.

The present invention is further directed to a process for preparing a substantially spherical supramolecular assembly having a substantially enclosed volume and a framework structure that mimics a Platonic or Archimedean solid. (The disclosure contained in MacGillivray et al. (*Nature* 389 469 (1997)) is hereby incorporated by reference.) The process comprises combining at least four synthons in a solvent in a proportion with the stoichiometry being based upon the following table, in which "c" represents th num (so that, e.g., "fe" is the number of three-sided faces):

| NAME | c | e | f3 | f4 | f5 | f6 | f8 | f10 |
|---|---|---|---|---|---|---|---|---|
| cube | 8 | 12 | — | 6 | — | — | — | — |
| octahedron | 6 | 12 | 8 | — | — | — | — | — |
| dodecahedron | 20 | 20 | — | — | 12 | — | — | — |
| icosohedron | 18 | 24 | 20 | — | — | — | — | — |
| truncated tetrahedron | 12 | 18 | 4 | — | — | 4 | — | — |
| truncated cube | 24 | 36 | 8 | — | — | — | 6 | — |
| truncated octahedron | 24 | 36 | — | 6 | — | 8 | — | — |
| cuboctahedron | 12 | 24 | 8 | 6 | — | — | — | — |
| small rhombicuboctahedron | 24 | 48 | 8 | 18 | — | — | — | — |
| great rhombicuboctahedron | 48 | 72 | — | 12 | — | 8 | 6 | — |
| snub cube | 24 | 60 | 32 | 6 | — | — | — | — |
| truncated dodecahedron | 60 | 90 | 20 | — | — | — | — | 12 |
| truncated icosahedron | 60 | 90 | — | — | 12 | 20 | — | — |
| icosidodecahedron | 30 | 60 | 20 | — | 12 | — | — | — |
| small rhombicosidodecahedron | 60 | 120 | 20 | 30 | 12 | — | — | — |
| great rhombicosidodecahedron | 120 | 180 | — | 30 | — | 20 | — | 12 |
| snub dodecahedron | 60 | 150 | 80 | — | 12 | — | — | — |

Other objects and features of this invention will be apparent and still others will be pointed out hereinafter.

BRIEF DESCRIPTION OF THE DRAWINGS

FIG. 3. The snub cube—one of the thirteen Archimedean solids. The square faces correspond to the calixarenes; the eight shaded triangles that adjoin three squares correspond to the water molecules of supramolecular assembly 1a.

DETAILED DESCRIPTION OF THE INVENTION

Definitions

Figure 1A:
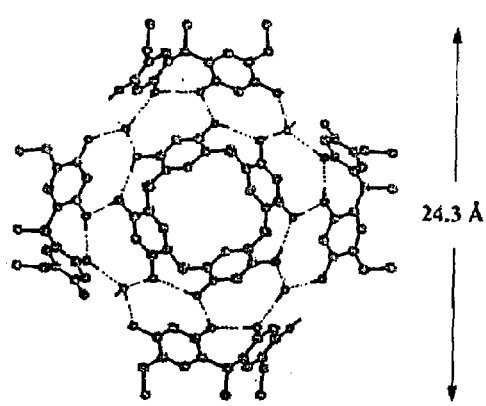
FIG. 1. The structure formed from 6 C-methylcalix[4]resorcinarenes (see 2a defined in FIG. 2 below)+8H2O, hereinafter referred to as "supramolecular assembly 1a" (1a) cross-sectional view; (1b) space filling views along the crystallographic 4-fold rotation axis; (1c) 3-fold rotation axis; (1d) 2-fold rotation axis; (1e) a cut-away view along the 3-fold rotation axis, (1f) solid state packing, where the shaded dark grey spheres also represent supramolecular assembly 1a (solvent molecules have been omitted for clarity)
Figure 1B:
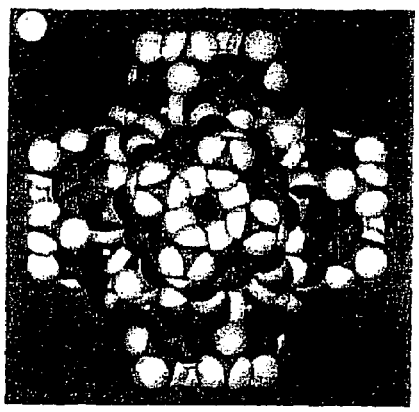
Figure 1C:
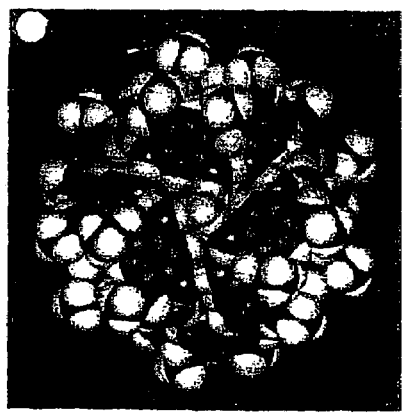
Figure 1D:
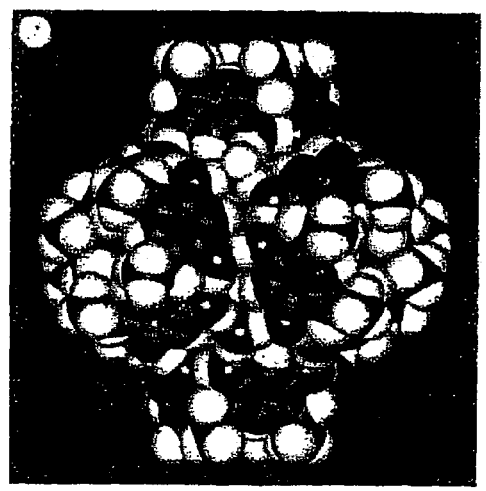
Figure 1E:
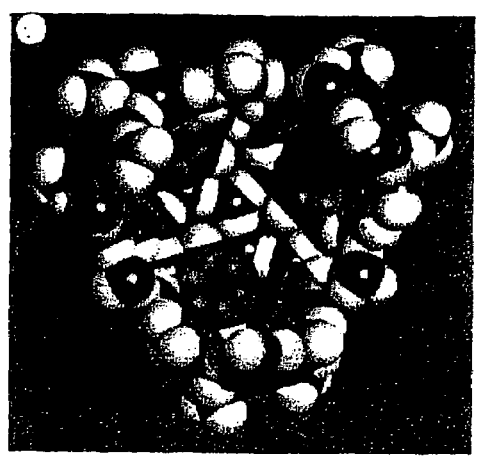

As used herein, the term "synthon" shall mean a molecular or ionic building block capable of interacting with itself or other molecular and/or ionic building blocks by way of non-covalent and/or coordinate covalent bonds.

The term "sub-unit" shall mean regular polygons and/or polygons that exhibit quasi-equivalence.

The term "quasi-equivalence" shall mean the relaxation of symmetry of regular polygons. The term "Ar" means aryl; "Ph" means phenyl; "Me" means methyl, and "R" means lower alkyl unless otherwise defined.

The term "substantially enclosed volume", as used herein means a volume located within the interior region of an supramolecular assembly, that may or may not be accessible by ions, molecules, or combinations of ions and/or molecules.

The term "substantially spherical" as used herein means an supramolecular assembly that possesses a surface that approximates the shape of a sphere such that its framework structure mimics a Platonic or Archimedean solid.

The term "Platonic solid" as used herein includes tetrahedrons, cubes, octahedron, dodecahedrons, and icosahedrons, and the term "Archimedean solid" as used herein includes truncated tetrahedrons, truncated cubes, truncated octahedrons, cuboctahedrons, small rhombicuboctahedrons, great rhomicuboctahedrons, snub cubes, truncated dodecahedrons, truncated icosahedrons, icosidodecahedrons, small rhombicosidodecahedrons, great rhombicosidodecahedrons, and snub dodecahedrons. These solids have the number of corners ("c"), edges ("e"), and faces ("f3, f4, f5, f6, f8, and f10") as indicated in the following table wherein "f3" means a three-sided face, "f4" means a four-sided face, etc.:

| NAME | c | e | f3 | f4 | f5 | f6 | f8 | f10 |
|---|---|---|---|---|---|---|---|---|
| cube | 8 | 12 | — | 6 | — | — | — | — |
| octahedron | 6 | 12 | 8 | — | — | — | — | — |
| dodecahedron | 20 | 20 | — | — | 12 | — | — | — |
| icosohedron | 18 | 24 | 20 | — | — | — | — | — |
| truncated tetrahedron | 12 | 18 | 4 | — | — | 4 | — | — |
| truncated cube | 24 | 36 | 8 | — | — | — | 6 | — |
| truncated octahedron | 24 | 36 | — | 6 | — | 8 | — | — |
| cuboctahedron | 12 | 24 | 8 | 6 | — | — | — | — |
| small rhombicuboctahedron | 24 | 48 | 8 | 18 | — | — | — | — |
| great rhombicuboctahedron | 48 | 72 | — | 12 | — | 8 | 6 | — |
| snub cube | 24 | 60 | 32 | 6 | — | — | — | — |
| truncated dodecahedron | 60 | 90 | 20 | — | — | — | — | 12 |
| truncated icosahedron | 60 | 90 | — | — | 12 | 20 | — | — |
| icosidodecahedron | 30 | 60 | 20 | — | 12 | — | — | — |
| small rhombicosidodecahedron | 60 | 120 | 20 | 30 | 12 | — | — | — |
| great rhombicosidodecahedron | 120 | 180 | — | 30 | — | 20 | — | 12 |
| snub dodecahedron | 60 | 150 | 80 | — | 12 | — | — | — |

The "hydrocarbon" moieties described herein (other than the hydrocarbon solvents) are organic radicals or substituents consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms.

The alkyl groups described herein are preferably lower alkyls containing from one to 20 carbon atoms in the principal chain and up to 40 carbon atoms. They may be straight or branched chain and include methyl, ethyl, propyl, isopropyl, butyl, hexyl, and the like. They may be substituted with aliphatic or other hydrocarbon radicals.

The alkenyl groups described herein are preferably lower alkenyl containing from two to 20 carbon atoms in the principal chain and up to 40 carbon atoms. They may be straight or branched chain and include ethenyl, propenyl, isopropenyl, butenyl, isobutenyl, hexenyl, eicosenyl, and the like. They may be substituted with aliphatic or other hydrocarbon radicals.

The alkynyl groups described herein are preferably lower alkynyl containing from two to 20 carbon atoms in the principal chain and up to 40 carbon atoms. They may be straight or branched chain and include ethynyl, propynyl, butynyl, isobutynyl, hexynyl, eicosynyl, and the like. They may be substituted with aliphatic or other hydrocarbon radicals.

The aryl moieties described herein have one to three rings, contain from 6 to 20 carbon atoms and include phenyl, biphenyl, naphthyl, anthracenyl, fluorene, acenaphthylene, and the like. They may be substituted with hydrocarbon radicals, heterosubstituted hydrocarbon, or hetero-atom containing substituents, with the hetero-atoms being selected from the group consisting of nitrogen, oxygen, silicon, phosphorous, boron, sulfur, and halogens. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido. Phenyl is the more preferred aryl.

The heteroaryl moieties described are heterocyclic compounds or radicals that are analogous to aromatic compounds or radicals and that contain a total of 5 to 20 atoms, usually 5 or 6 ring atoms, and at least one atom other than carbon, such as furyl, thienyl, pyridyl and the like. The heteroaryl moieties may be substituted with hydrocarbon, heterosubstituted hydrocarbon or hetero-atom containing substituents with the hetero-atoms being selected from the group consisting of nitrogen, oxygen, silicon, phosphorous, boron, sulfur, and halogens. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido.

The heterosubstituted hydrocarbon moieties described herein are hydrocarbon moieties that are substituted with at least one atom other than carbon, including moieties in which a carbon chain atom is substituted with a hetero atom such as nitrogen, oxygen, silicon, phosphorous, sulfur, or a halogen atom. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido.

Description

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

In accordance with the present invention, it has been discovered that spherical assemblies that resemble the five Platonic solids and the thirteen Archimedean solids can be prepared from at least four synthons and a combination of covalent bonding, non-covalent bonding, and coordinate covalent bonding. At least two of the bonds must be selected from non-covalent bonds, coordinate covalent bonds, or a combination thereof.

In general, the synthons may be simple organic or inorganic molecules, or may be complex organic or inorganic superstructures. Several synthons are suitable for use with the present invention. Suitable synthons include:

1) calixarenes containing 4–8 arene units, preferably arene units corresponding to the structure

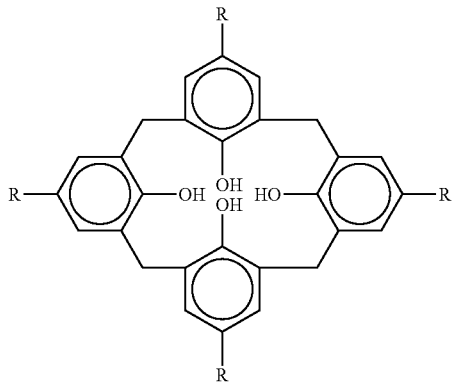

wherein R is hydrocarbon, heterosubstituted hydrocarbon, heteroaryl, —$NO_2$, phenyl, biphenyl, —$NH_2$, —$SO_3^-$, —COOH, —COOR", H, Cl, Br, I, or pyridyl, and R" hydrocarbon, heterosubstituted hydrocarbon, heteroaryl, or phenyl;

2) Calixresorcinarenes, with calix[4]resorcinarene being preferred and corresponding to the structure

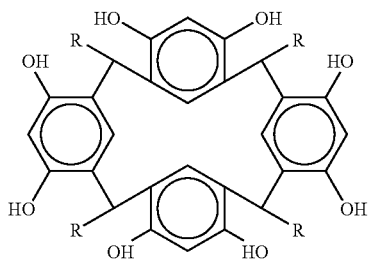

wherein R is hydrocarbon, heterosubstituted hydrocarbon, or heteroaryl;

3Z) Cyclotricatechylene and cyclotriveratrylene, corresponding to the structure

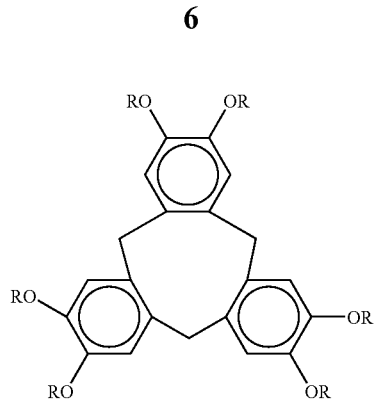

wherein R is H for cyclotricatechylene and R is Me for cyclotriveratrylene.

4) Cyclotetracatechylene and cyclotetraveratrylene, corresponding to the structure

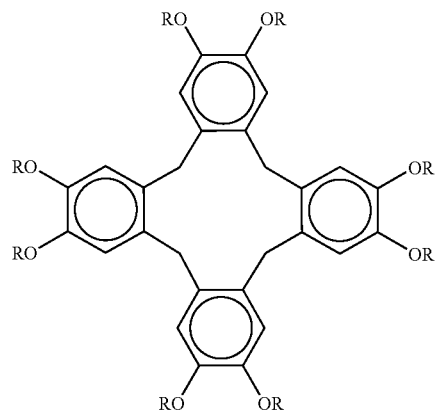

wherein R is H for cyclotetracatechylene and R is Me for cyclotetraveratrylene.

5) Naphthalene-based calixarenes according to the general formula

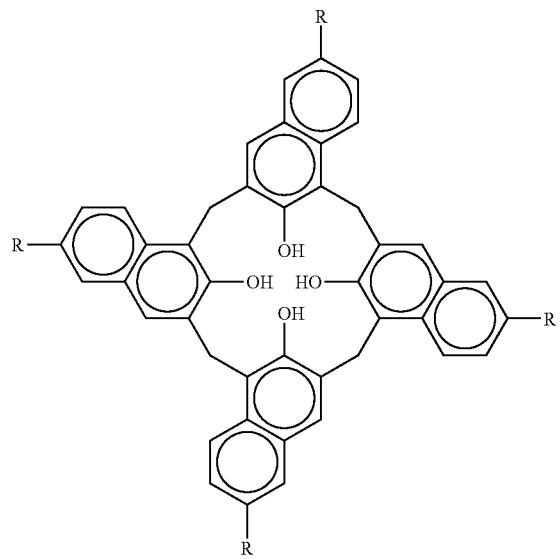

wherein R is hydrocarbon, heterosubstituted hydrocarbon, heteroaryl, —$NO_2$, —$NH_2$, —$SO_3^-$, —COOH, —COOR", H, Cl, Br, I, or pyridyl, and R" is hydrocarbon, heterosubstituted hydrocarbon, heteroaryl, or phenyl;

6) Multifunctional carboxylic acids according to the general formula

wherein n is an integer taking the values 2–6 and X is COOH, and including but not limited to the preferred 1,3,5-benzenetricarboxylic acid, 1,2-benzenedicarboxylic acid, 1,3-benzenedicarboxylic acid, 1,4-benzenedicarboxylic acid, 1,2,4,5-benzenetetracarboxylic acid, and 1,2,3,4,5,6-benzenehexacarboxylic acid;

7) Multifunctional esters according to the general formula

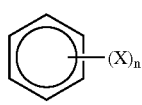

wherein n is an integer taking the values 2–6 and X is COOR, wherein R is hydrocarbon or heterosubstituted hydrocarbon, and including but not limited to the preferred 1,3,5-benzene ester, 1,2-benzene ester, 1,3-benzene ester, 1,4-benzene ester, 1,2,4,5 -benzene ester, and 1,2,3,4,5-benzene ester;

8) Multifunctional alcohols according to the general formula:

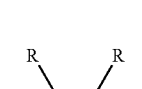

wherein n is an integer taking the values 2–6 and X is OH, and including but not limited to the preferred 1,3,5-benzenetriol, 1,2-benzenediol, 1,3-benzenediol, 1,4-denzendiol, 1,2,4,5,-benzenediol, 1 1,2,4,5-benzenetraol;

9) Porphyrins, both metal substituted and metal free according to the general formula:

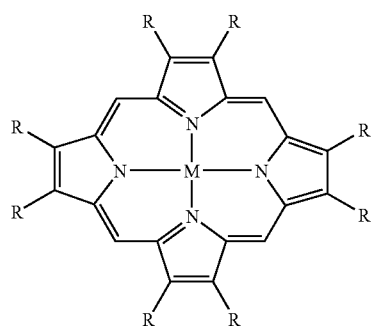

wherein the R groups are the same or different and may be H, hydrocarbon, hydrocarbon substituted heteroaromatic, pyridyl, or the like, and M is two $H^+$ or a metallic element with atomic number Z of 14–15, 21–33, 39–51, 57–83, or 90–103;

10) Bidentate pyridine based bridging ligands including but not limited to

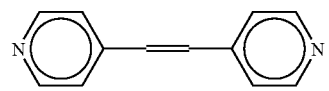

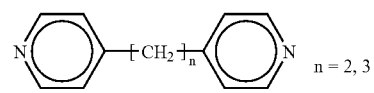

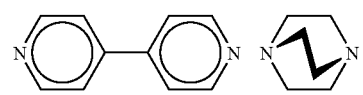

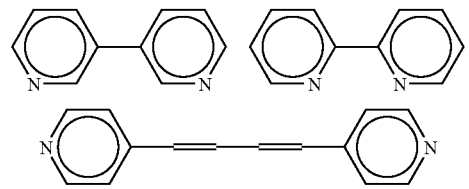

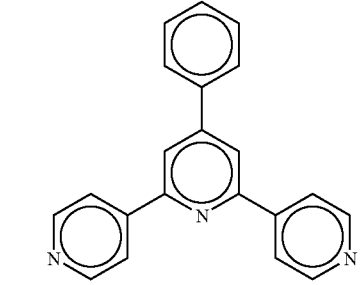

11) Tridentate pyridine based bridging ligands including but not limited to

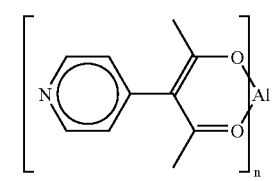

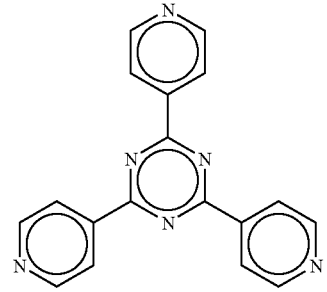

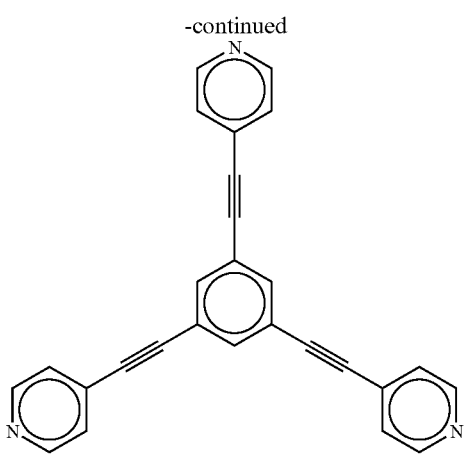

wherein n is an integer taking the values 1–3;

12) Tetradentate pyridine based bridging ligands including but not limited to

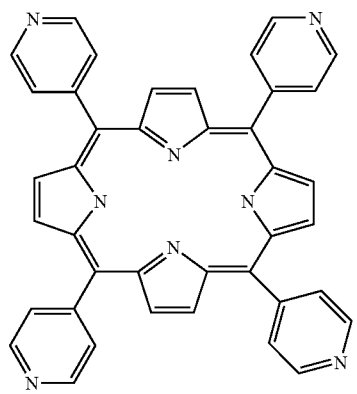

13) Alcohols including methanol, ethanol, propanol, isopropanol, phenol, and ROH where R is hydrocarbon or heterosubstituted hydrocarbon;

14) Water;

15) Transition metals, lanthanides, actinides, or Group II, III, IV, or V metals;

16) Organometallic fragments, such as facially substituted transition metals with carbonyl ligands, or arene or cyclopentadienyl-coordinated transition metals;

17) Coordination compounds of transition and non-transition metals that contain ligands capable of hydrogen bond donor or acceptor properties, including but not limited to

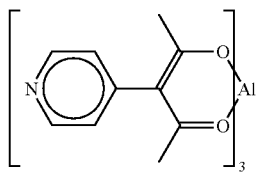

wherein the metal substituted may include transition metals, or Group II, III, or IV metals and n is an integer taking the values 1–3.

We refer generically to the calixarenes, calixresorcinarenes, cyclotriveratrylene, cyclotricatechylene, and naphthalene-based calixarenes of the present invention as "cyclic calix-type compounds," and refer to the arene portion whether substituted or unsubstituted as "Z."

It should be noted that combination components, or hybrids of two or more of the above listed synthons are also suitable synthons with the present invention.

In general, there are two types of non-covalent interactions or bonds that may be used to bond the synthons: non-directional and directional. Although directional bonds are preferred for the construction of closed surface substantially spherical assemblies, non-directional bonds (electrostatic type) may be useful. The possible combinations are ion-ion, ion-dipole, ion-induced dipole, dipole-dipole, dipole/induced dipole and induced dipole-induced dipole. See, e.g., "Physical Methods in Inorganic Chemistry" by R. S. Drago, Reinhold Publishing Corp., New York, 1965, p.68ff., which is incorporated herein by reference). Also included in this classification are π-stacking interactions. Van der Waals interactions may also be employed.

Of the various types of directional bonds, hydrogen bonds are preferred and the most preferred of these are O—H . . . O, N—H . . . O, O—H . . . N, F—H . . . F, F—H . . . O, O—H . . . F, F—H . . . N, and N—H . . . F. Other hydrogen bonds such as C—H . . . F, C—H . . . O, C—H . . . N, C—H . . . Cl, C—H . . . S, C—H . . . Br, C—H . . . I, O—H . . . Cl, O—H . . . Br, O—H . . . I, N—H . . . Cl, N—H . . . Br, N—H . . . I, S—H . . . O, S—H . . . N, and S—H . . . F may, nevertheless, be used.

In the preferred supramolecular assembly utilizing hydrogen bonds, the synthons must be hydrogen bond donors (e.g., N—H), hydrogen bond acceptors (e.g., O), or an appropriate combination of hydrogen bond donors and hydrogen bond acceptors (e.g., O) and the other synthons must be hydrogen bond acceptors, hydrogen bond donors (e.g., N—H), or an appropriate combination of hydrogen bond donors and hydrogen bond acceptors.

The choice of synthons involves the selection of synthons that provide a means by which the edge-sharing faces of the Platonic or Archimedean solids are bonded together.

When a combination of synthons with the appropriate hydrogen bonding ability has been selected, consideration is preferably given to steric interactions. If the van der Waals volume of an atom or atoms on one synthon is required to occupy the same space as the van der Waals volume of an atom or atoms on another synthon, the combination is inoperative.

The molecular or ionic supramolecular assembly of the present invention is prepared by combining the synthons in the required stoichiometric ratio in a solvent. Time and temperature do not provide limitations on the process. However, the assemblies may be affected by extraordinary high temperature. The crystallization is preferably carried out at between about 15 and about 25° C.

The solvent in which the synthons are mixed does not appear to be narrowly critical. The synthons may be combined in one or more of the following solvents: hydrocarbon based such as hexane, heptane, benzene, or toluene; halogenated hydrocarbons such as chloroform, carbon tetrachloride, or methylene chloride; nitromethane, nitrobenzene, acetone, tetrahydrofuran, MIBK, DMSO, DMF, propylene carbonate, acetonitrile, methanol, ethanol, propanol, isopropanol, pyridine, and water. The hydrogen-bonding ability of the solvent, however, must not interfere with that of the supramolecular assembly.

In accordance with the present invention, a chiral supramolecular assembly 1a that consists of six C-methylcalix[4]resorcinarenes and eight water molecules and is held together by 60 hydrogen bonds is illustrated in FIG. 1a. This supramolecular assembly has been found to maintain its structure in apolar media and encapsulate guest species within a well-defined cavity that possesses an internal volume of 1375 Å$^3$. Single crystal X-ray analysis has revealed the topology of supramolecular assembly 1a to resemble a spherical virus and conform to the structure of a snub cube, one of the thirteen Archimedean solids (Wenninger, *Polyhedron Models*, Cambridge University Press, New York, 1971, the disclosure of which is incorporated by reference).

Co-crystallization studies of C-methylcalix[4]resorcinarene with hydrogen bond acceptors in aromatic solvents have revealed the ability of C-methylcalix[4]resorcinarene to self-assemble as a spherical hexamer, along with adventitious water molecules to form supramolecular assembly 1a. In a preferred method, the water is added in a stoichiometric amount. Solution studies have revealed the ability of C-undecylcalix[4]resorcinarene to maintain a structure analogous to that of supramolecular assembly 1a in apolar organic solvents.

Addition of C-methylcalix[4]resorcinarene (0.015 g) to a boiling aliquot of neat nitrobenzene (5 mL) followed by cooling to room temperature yielded light yellow cubic crystals suitable for X-ray analysis. The formulation of this compound was confirmed by single-crystal X-ray diffraction and $^1$H NMR spectroscopy.

A cross sectional view of the X-crystal structure of supramolecular assembly 1a is shown in FIG. 1. The supramolecular assembly consists of six molecules of C-methylcalix[4]resorcinarene and eight molecules of water that have assembled, via 60 O—H...O hydrogen bonds, to form a shell-like cubic spheroid. The calixarenes, each of which lies around a four-fold axis, point their hydroxyl groups along the periphery of supramolecular assembly 1a and form two hydrogen bonds to two neighboring calixarenes while the water molecules, each of which lies on a three-fold axis, are embedded along the surface of supramolecular assembly 1a such that they lie on the vertices of a cube (edge length=9.00 Å) and participate in three hydrogen bonds with three different calixarenes. Notably, each calixarene also exhibits four intramolecular hydrogen bonds, one at each of its corners, which impart stability to its bowl-like conformation. As a result, as shown in FIGS. 1b–d, supramolecular assembly 1a possesses 4 3 2 symmetry, ignoring all hydroxyl hydrogen atoms, and a well-defined central cavity with a maximum diameter of 17.7 Å and an internal volume of 1375 Å$^3$, as illustrated in FIG. 1e. Indeed, the cavity of supramolecular assembly 1a is vast, being more than 4.5 times larger than the cavity of the largest molecular capsule reported to date (ca. 300 Å$^3$). Interestingly, the calixarenes of supramolecular assembly 1a are twisted by 230 with respect to the faces of the water "cuboid" which, as a consequence, makes supramolecular assembly 1a chiral.

Figure 1F:
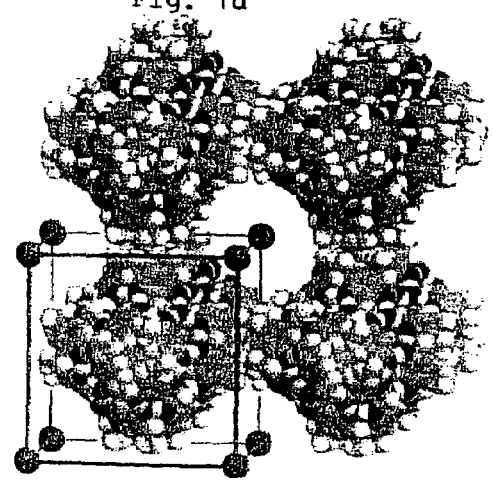
Figure 2:
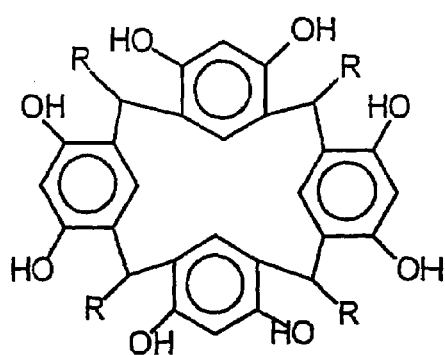
FIG. 2. Molecular structures of calix[4]resorcinarene (2); C-methylcalix[4]resorcinarene (2a); C-undecylcalix[4]resorcinarene (2b).

Supramolecular assembly 1a self-assembles in the solid state such that neighboring spheroids fall on their four-fold axes and their methyl groups lie staggered owing to the twisting displayed by the macrocycles, as shown in FIG. 1f. This gives rise to an interpenetrating body-centered cubic lattice that exhibits interstices within supramolecular assembly 1a that are occupied by disordered water and nitrobenzene molecules. Despite being able to locate guest species within the interior of supramolecular assembly 1a (i.e. electron density maxima), it is not possible to determine their identity from the X-ray experiment presumably due to the high symmetry imposed by supramolecular assembly 1a and high thermal motion within the cavity.

Figure 3:
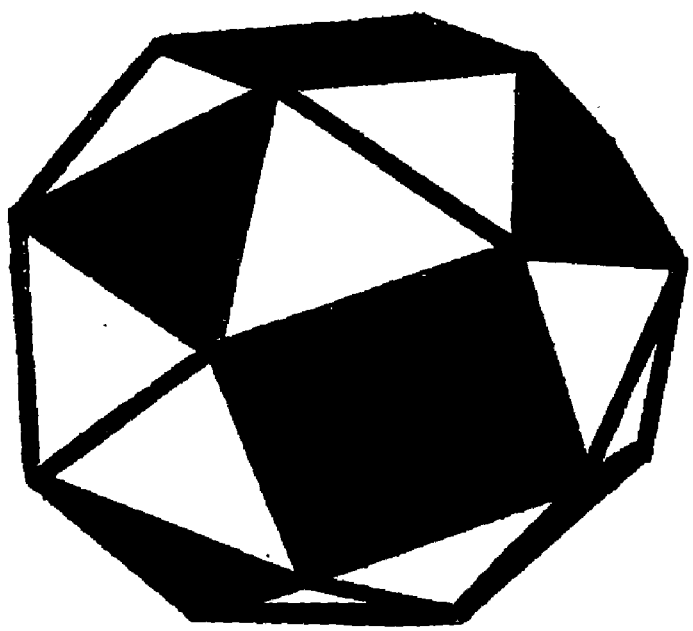

Polyhedron models revealed the structure of supramolecular assembly 1a to conform to a snub cube (FIG. 3), one of the thirteen Archimedean solids, in which the vertices of the square faces correspond to the corners of the calixarenes and the centroids of the eight triangles that adjoin three squares correspond to the eight water molecules. It is clear to us that calixarenes and water molecules are not essential for the formation of the chemical version of the snub cube. Any molecules or ions with square and triangular symmetry, respectively, that can be bonded together by hydrogen bonds or other interactions will also form the chemical version of the snub cube. Indeed, the ability of six calixarenes and eight water molecules to self-assemble to form supramolecular assembly 1a is reminiscent of spherical viruses in which identical copies of proteins self-assemble, via noncovalent forces, to form viral capsids having icosahedral cubic symmetry and a shell-like enclosure. In fact, supramolecular assembly 1a is the first example of a closed surface supramolecular spheroid that possesses n>3 sub-units and, owing to the fit exhibited by its components, possesses a topology that agrees with the theory of virus shell structure, which states that octahedral systems must contain 24 asymmetric units and possess 4 3 2 symmetry. Moreover, such observations illustrate that in order to design related hosts, one must consider the limited number of possibilities available in space for such frameworks, those being the five Platonic (regular) solids and the thirteen Archimedean (semi-regular) solids. The ramifications of these observations are important since they suggest that appropriately sized, shaped, and functionalized components may be selected, a priori, to design similar spherical hosts in a similar way to the self-supramolecular assembly exhibited by supramolecular assembly 1a.

The hydrogen bond pattern that holds supramolecular assembly 1a together is complex. Although the hydroxyl hydrogen atoms were not locateable, it is possible to deduce the pattern knowing the positions and numbers of hydrogen bond donors and acceptors. In principle, 64 hydrogen bond donors and 112 hydrogen bond acceptor sites are available to form supramolecular assembly 1a: eight donors and sixteen acceptor sites from each calixarene and two donors and two acceptor sites from each water molecule. There are, however, two restrictions that arise from the positions of these sites that require the number of hydrogen bonds that define supramolecular assembly 1a to equal 60 which, as a result, cause four hydroxyl hydrogen atoms to point away from its surface. The first restriction lies in the positions of the eight water molecules. Their location on the three fold axes limits the number of hydrogen bonds in which the water molecules can participate that contributes to supramolecular assembly 1a to 24; in other words, each water molecule is capable of participating in only three hydrogen bonds along the surface of supramolecular assembly 1a and is therefore unable to use its two hydrogen bond donors and two hydrogen bond acceptor sites, simultaneously, to form supramolecular assembly 1a. The second restriction arises from the presence of the four intramolecular hydrogen bonds at the corners of the calixarenes. In particular, these interactions force four hydroxyl groups to point their hydrogen atoms above each macrocycle which, as a consequence, makes each calixarene a quadruple hydrogen bond donor. (MacGillivray et al. *J. Am. Chem. Soc.*, 119 6931 (1997), the disclosure of which is incorporated by reference.) Since each calixarene uses two of these hydrogen atoms to form hydrogen bonds to two calixarenes, this leaves two hydroxyl hydrogen atoms per calixarene which are, subsequently, used to form 12 hydrogen bonds to the water molecules. Consequently, the water molecules must use 12 of their hydrogen bond acceptor sites to form these hydrogen bonds and, owing to their position on the three fold axes, must position four hydrogen atoms, each from a different water molecule, away from the surface of supramolecular assembly 1a. To complete the hydrogen bond array, the water molecules use 12 hydrogen atoms to form 12 hydrogen bonds to 12 hydrogen bond acceptor sites located on the calixarenes.

Figure 4A:
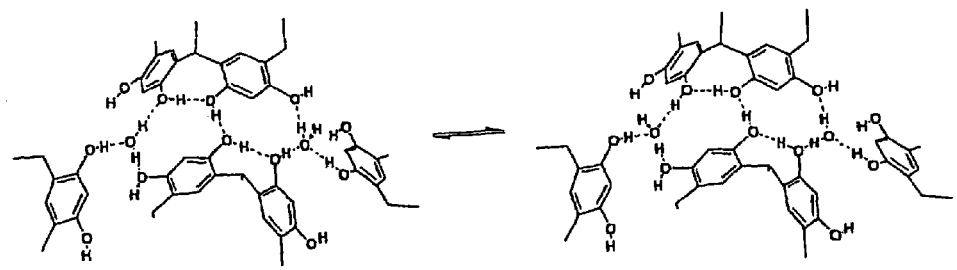
FIG. 4. The hydrogen bond pattern of supramolecular assembly 1a: (a) the five hydrogen bonds that comprise each "edge" of the water cuboid, (b) $D_{2d}$ symmetry representation of the water cuboid, (c) the three calixarene conformers that are associated with the faces of the water cuboid.

A closer inspection of the hydrogen bond pattern of supramolecular assembly 1a reveals that each "edge" of the water cuboid consists of a polar chain of five cooperative hydrogen bonds, as shown in FIG. 4a.

As a result, each edge is capable of changing the sense of its direction via interconversion of two water molecules from a hydrogen bond donor to a hydrogen bond acceptor and vice versa. Furthermore, since four water molecules point four hydrogen atoms away from the surface of supramolecular assembly 1a, the edges of the cuboid are capable of undergoing such proton rearrangements simultaneously, which, in effect, makes supramolecular assembly 1a a spherical proton pump able to channel the four "dangling" protons to the eight corners of the water cuboid.

Figure 4B:
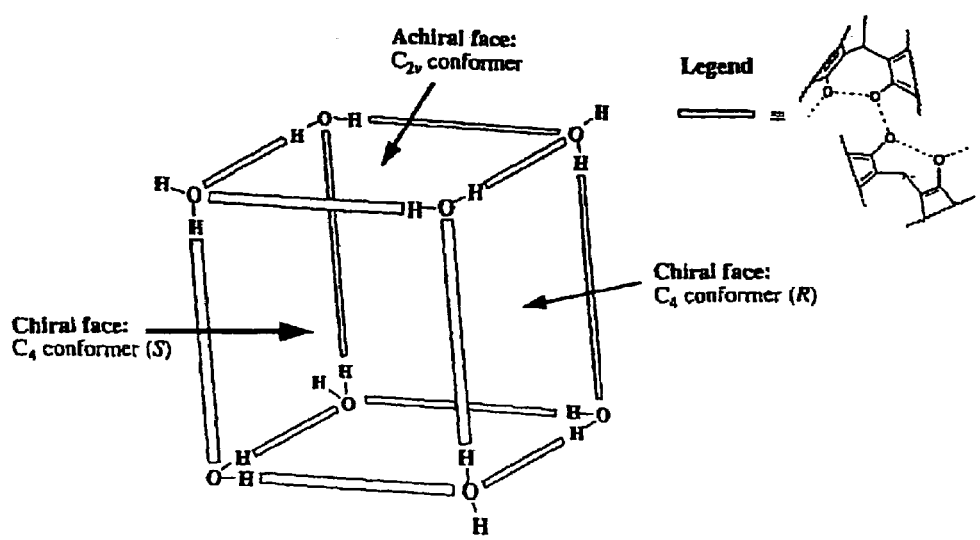
Figure 4C:
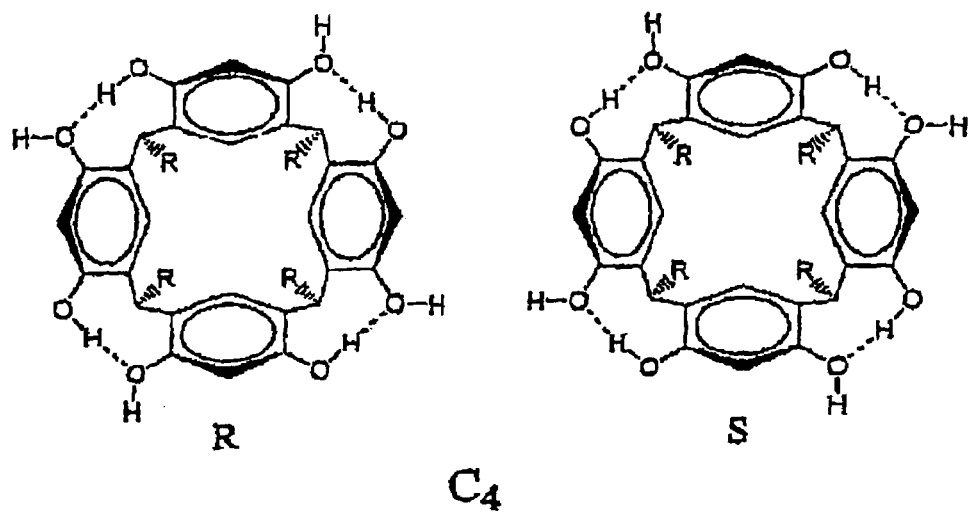
Figure 4C:
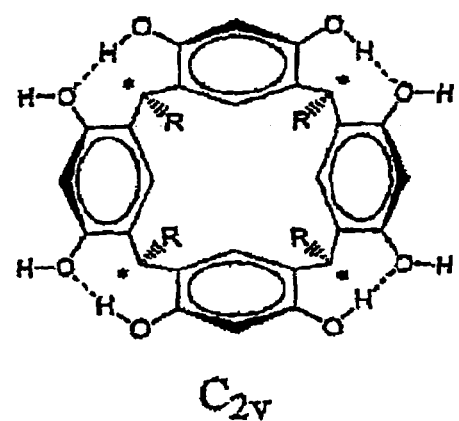

Although each of the dangling protons may be placed at any one of the eight corners, it is most convenient, for symmetry reasons, to place them at the vertices of a tetrahedron such that the water cuboid, ignoring the calixarenes, possesses D2d symmetry, as shown in FIG. 4b. (Wales et al. *J. Chem. Phys.* 98, 7257–7268 (1993), the disclosure of which is incorporated by reference). This arrangement furnishes the cuboid with four chiral faces and two achiral faces which, upon completing the five hydrogen bonds along each edge, gives rise to three distinct calixarenes, two of which are chiral ($C_4$) and one of which is achiral ($C_{2v}$), as shown in FIG. 4c. Notably, the chiral calixarenes are associated with the chiral faces such that their handedness match while the achiral calixarenes are associated with the achiral faces. As a consequence of this arrangement, supramolecular assembly 1a possesses $D_2$ symmetry.

Figure 5:
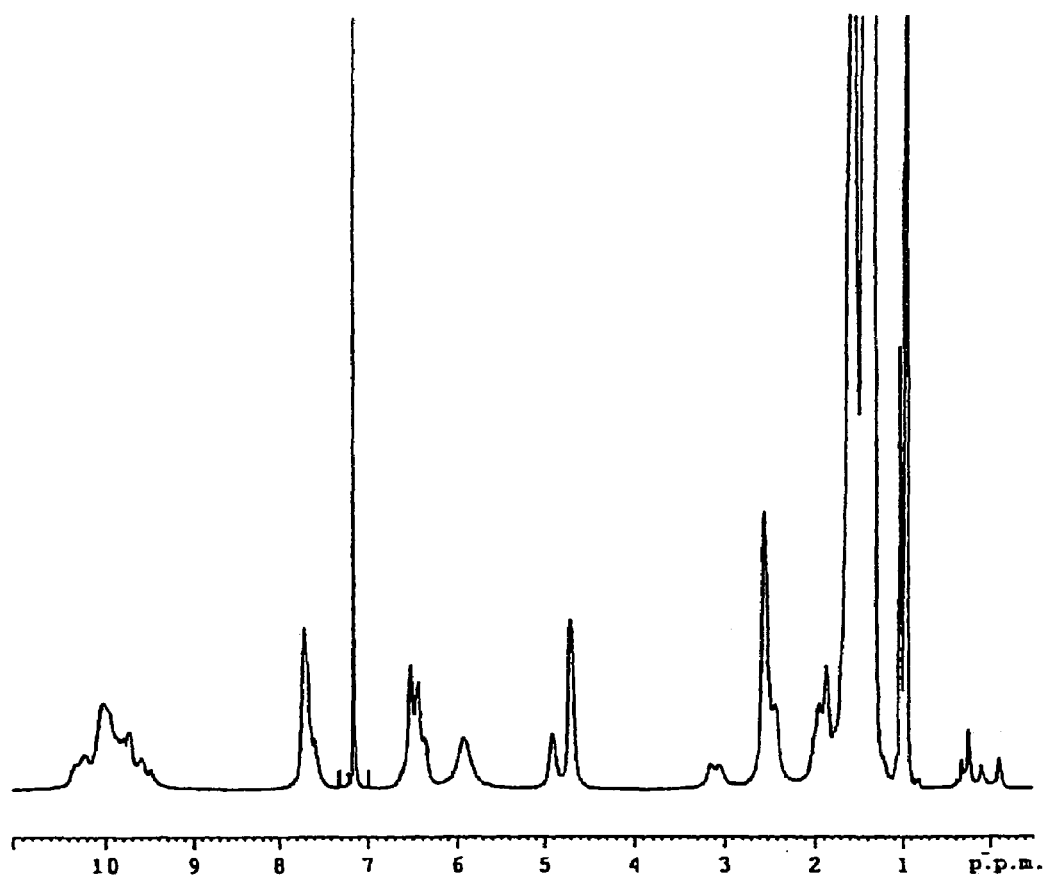
FIG. 5. 500 MHz $^1$H NMR spectrum of C-undecylcalix [4]resorcinarene in benzene-$d_6$.
Figure 6:
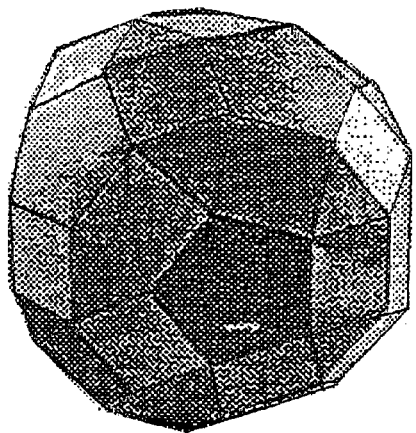
FIG. 6 illustrates a rhombicosidodecahedron as prepared in Example 3.
Figure 7:
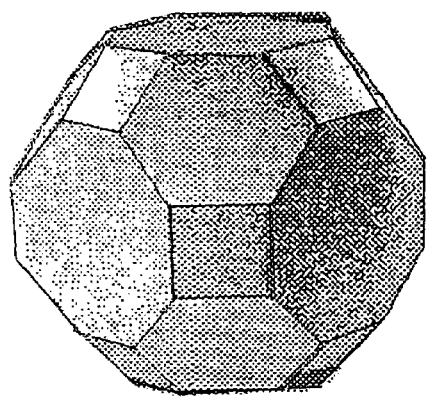
FIG. 7 illustrates a rhombitruncated cuboctahedron as prepared in accordance with Example 4.
Figure 8:
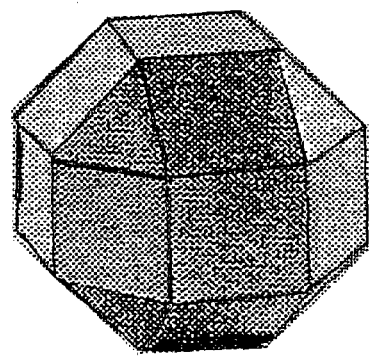
FIG. 8 illustrates a rhombitruncated cuboctahedron as prepared in accordance with Example 5.

Evidence supporting the ability of C-undecylcalix[4]resorcinarene to maintain the structure of compound 1a in solution has been obtained via 1D and 2D $^1$H NMR measurements. Indeed, the spectrum of of C-undecylcalix-[4]resorcinarene in benzene-$d_6$ displays resonances attributed to the chiral and achiral calixarenes as well as the water molecules that make up compound 1a, as shown in FIG. 5. In particular the CH hydrogen atoms of the bridging methines, at $3.7 \times 10^{-3}$ M, exhibit two broad singlets at 4.69 and 4.90 ppm (relative intensities 2:1) while their $\alpha$-CH$_2$ hydrogens exhibit a broad singlet at 2.52 ppm and a pair of broad multiplets at 2.50 and 3.31 ppm (relative intensities 4:1:1). These splittings and line broadening effects are consistent with the presence of appreciably populated $C_4$ and $C_{2v}$ conformers undergoing concerted hydrogen-bond tunneling motions in which the singlet at 4.90 ppm and the two multiplets at 2.50 and 3.31 ppm are assigned to the $C_{2v}$ conformer owing to the presence of chiral methane carbon atoms that induce desymmetrization of the methylene protons. That the multiplets are coupled with the singlet at 4.90 ppm, as well as with each other, was verified by COSY NMR data. Furthermore, a broad singlet that shifts downfield with increasing concentration and integrates to 12 protons is observed at 5.91 ppm and is assigned to the 12 protons of the water molecules that contribute to supramolecular assembly 1a. This assignment is also supported by $D_2O$ exchange experiments. Indeed, these observations, coupled with a recent molecular mass determination by vapor pressure osmometry in benzene (7066 g mol$^{-1}$),(Aoyama et al. *J. Am. Chem. Soc.* 111, 5397–5404 (1989), the disclosure of which is incorporated by reference) provide convincing evidence supporting the ability of C-undecylcalix[4]resorcinarene to maintain the structure of compound 1a in solution.

Our discovery that C-methylcalix[4]resorcinarene and of C-undecylcalix[4]resorcinarene form spherical molecular assemblies could bear relevance in a number of areas. In addition to providing new insight into design criteria for the construction of spherical hosts, that supramolecular assembly 1a sustains its cavity in both solution and the solid state suggests that supramolecular assembly 1a could be exploited to package guests within its interior. This could lead to a number of applications such as supramolecular assembly 1a as: (1) a chiral catalyst for chemical transformations,(2) a catalyst for chemical transformations, (3) a medium for chemical transformations,(4) materials with beneficial magnetic, optical, or electric properties, (5) a microvesicle for drug delivery to mammals,(Mathiowitz et al. *Nature* 386, 410–414 (1997), the disclosure of which is incorporated by reference) and (6) an intermediate for separations problems. (Atwood et al. *Nature*, 368, 229–231 (1994), the disclosure of which is incorporated by reference) Indeed, molecular modeling experiments with fragments obtained from the Cambridge Structural Database illustrate that the interior of supramolecular assembly 1a is spacious enough to accommodate relatively large substrates such as coordination compounds (e.g. $ML_n$ where n is an integer taking the values 1–6), fullerenes (e.g. $C_{60}$), and supramolecular hosts (e.g. porphyrins). Considering the current commercial availability of C-methylcalix[4]resorcinarene and of C-methylcalix[4]resorcinarene, supramolecular assembly 1a may now be recognized as a readily available spheroid in a burgeoning area of spherical host chemistry. A specific example is in the delivery of a therapeutic or diagnostic agent to a mammal. This is a accomplished by forming a supermolecular assembly comprising the therapeutic or diagnostic agent and administering the supramolecular assembly comprising the agent to the mammal in sufficient quantities to be therapeutically or diagnostically useful.

The following examples illustrate the invention

EXAMPLE 1

Addition of C-methylcalix[4]resorcinarene (0.015 g) to a boiling aliquot of neat nitrobenzene (5 mL) followed by cooling to room temperature yielded light yellow cubic crystals suitable for X-ray analysis. The formulation of supramolecular assembly 1a was confirmed by single-crystal X-ray diffraction and $^1$H NMR spectroscopy.

EXAMPLE 2

Preparation of the cube.

8 PhH + 8 Ru + 12 4,4'-bipyridine ⟶

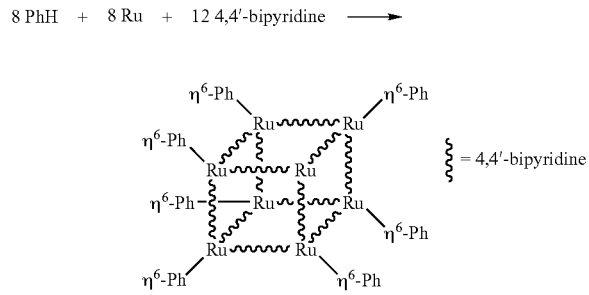

wherein the Ru atoms are linked together by the 4,4'-bipyridine synthons by coordinate covalent bonds.

EXAMPLE 3

Preparation of the rhombicosidodecahedron.

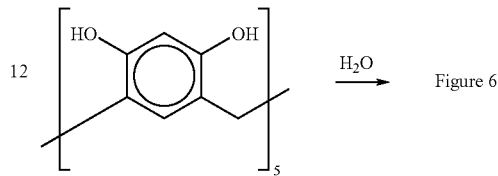

wherein the calix[4]resorcinarene synthons are bonded via O—H . . . O hydrogen bonds from one of the said synthons to the other said synthons.

EXAMPLE 4

Preparation of the rhombitruncated cuboctahedron.

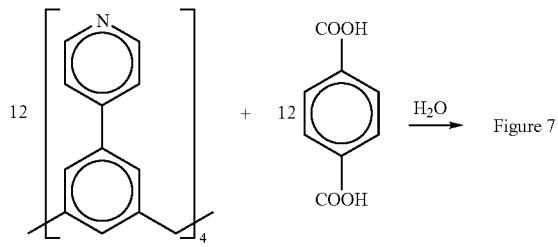

wherein a substituted calix[4]arene lies on each square face and the calixarenes are bridged by the 1,4-benzene dicarboxylic acid synthons. The hexagonal faces are formed from an edge from each of three calixarene synthons and three 1,4-benzene dicarboxylic acid synthons. The octagonal faces are formed from an edge from each of four calixarene synthons and four 1,4,benzene dicarboxylic acid synthons.

EXAMPLE 5

Preparation of the rhombicuboctahedron.

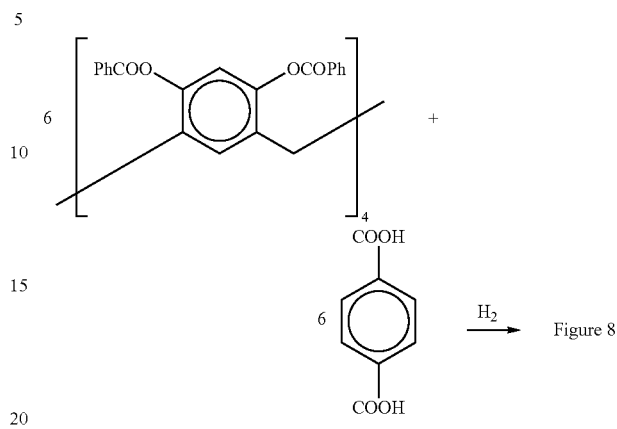

wherein the substituted calix[4]resorcinarenes lie on every other square face and said square faces are linked through hydrogen bonds by the 1,4-benzene dicarboxylic acid synthons.

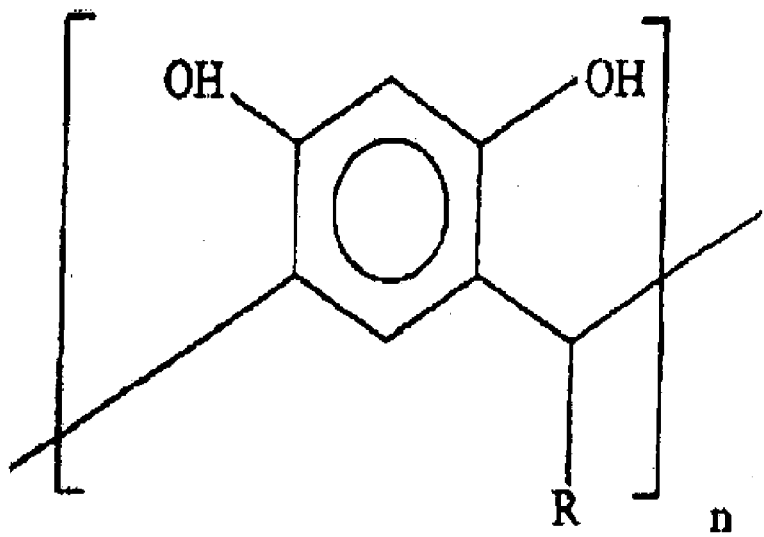

What is claimed is:

1. A substantially spherical molecular or ionic synthon assembly having a substantially enclosed volume greater than 1300 Å$^3$ and comprising six calix[4]resorcinarenes and eight water molecules as the synthons, the assembly mimicking a snub cube.

2. A substantially spherical supramolecular assembly having a substantially enclosed volume and a framework structure that mimics a Platonic or Archimedean solid, the supramolecular assembly comprising more than four synthons held together by a combination of carbon-based covalent, non-covalent, and/or coordinate covalent bonds, with at least two of the bonds being selected from the group consisting of noncovalent bonds and coordinate covalent bonds, wherein the synthons comprise cyclic calix-type compounds wherein the cyclic calix-type compound is a calixresorcinarene of the formula:

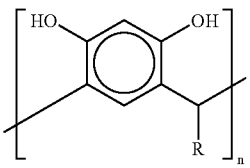

wherein n is an integer taking the values 4–8 and the R groups are independently selected from the group consisting of hydrocarbon, heterosubstituted hydrocarbon, and heteroaryl groups.

3. The assembly of claim 2 wherein said substantially spherical supramolecular assembly comprises six of said calix[4]resorcinarenes.

4. The assembly of claim 3 wherein said spherical supramolecular assembly comprises six C-methylcalix[4]resorcinarenes.

5. The assembly of claim 3 wherein said spherical assembly comprises six C-undecylcalix[4]resorcinarenes.

6. A substantially spherical molecular assembly comprising a hexamer of a calyx[4]resorcinarene characterized by the formula:

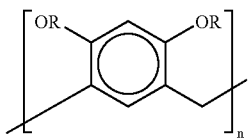
wherein R is a hydrocarbyl, heterosubstituted hydrocarbon, or heteroaryl group.
7. The spherical assembly of claim 6 having an enclosed interior volume greater than 1300 angstrums.
8. The spherical assembly of claim 7 in which R is hydrogen.
9. The spherical assembly of claim 7 in which R is methyl.
10. The spherical assembly of claim 7 in which R is undecyl.
* * * * *

UNITED STATES PATENT AND TRADEMARK OFFICE
CERTIFICATE OF CORRECTION

PATENT NO. : 7,169,957 B2
APPLICATION NO. : 10/408605
DATED : January 30, 2007
INVENTOR(S) : Jerry L. Atwood and Leonard R. MacGillivray It is certified that error appears in the above-identified patent and that said Letters Patent is hereby corrected as shown below:

The title page should be deleted to appear as per attached title page.

Column 16, Line 54--insert the words --hydrogen or-- between the words "from" and "the".

Column 16, Line 66--replace the word "calyx" with the word --calix--.

Please amend Column 17 as follows:

Column 17, Line 8--please insert the words --hydrogen or-- after the word "is" and before the word "a".

Column 17, Line 8--please insert the wording --and n is 6.-- after the word "group".

Signed and Sealed this

Twenty-sixth Day of January, 2010

David J. Kappos
*Director of the United States Patent and Trademark Office*

United States Patent
Atwood et al.

(10) Patent No.: US 7,169,957 B2
(45) Date of Patent: Jan. 30, 2007

(54) SUBSTANTIALLY SPHERICAL SUPRAMOLECULAR ASSEMBLIES

(76) Inventors: Jerry L. Atwood, 5704 S. Short Line Dr., Columbia, MO (US) 65203; Leonard R. MacGillivray, 103 Oberlin St., Iowa City, IA (US) 52245

(*) Notice: Subject to any disclaimer, the term of this patent is extended or adjusted under 35 U.S.C. 154(b) by 0 days.

(21) Appl. No.: 10/408,605

(22) Filed: Apr. 7, 2003

(65) Prior Publication Data
US 2004/0014963 A1 Jan. 22, 2004

Related U.S. Application Data

(63) Continuation of application No. 09/319,136, filed on Nov. 9, 1999, now abandoned.

(51) Int. Cl.
*C07C 39/12* (2006.01)
(52) U.S. Cl. .................................. 568/719; 568/720
(58) Field of Classification Search ............ 568/719, 568/720
See application file for complete search history.

(56) References Cited

OTHER PUBLICATIONS

Leonard R. MacGillivray and Jerry L. Atwood□□A Chiral sperical molecular assembly held together by 60 hydrogen bonds□.□□Nature 389, 469-472 (Oct. 2, 1997).. 1 1*
Peter Timmerman, Willem Verboom, Frank C.J.M. van Veggel, John P.M. van Duynhoven and David N. Reinhoudt□□A Novel Type of Stereoisomerism in Calix[4]arene-Based Carceplexes□□□□Angew. Chem. Int. Ed. Engl. 1994,33,No 22 pp. 2345-2348 *
Peter Timmerman, Willem Verboom, Frank C.J.M. van Veggel, Willem P. van Hoorn, and David N. Reinhoudt□□An Organic Molecule with a Rigid Cavity of Nanosize Dimensions□□□□Angew. Chem. Int. Ed. Engl. 1994,33,No. 12 pp 1292-1294 *

* cited by examiner

*Primary Examiner*—Johann Richter
*Assistant Examiner*—Lalitha Nagubandi
(74) *Attorney, Agent, or Firm*—William D. Jackson; Schultz & Associates, P.C.

(57) ABSTRACT

Disclosed are the general principles upon which closed molecular or ionic structural frameworks may be prepared. These frameworks are based upon the self-assembly (wherein the term self-assembly refers to the association of chemical components through inter-component bonds) of n>4 subunits where surface curvature is supplied by edge sharing of subunits.

10 Claims, 7 Drawing Sheets